United States Patent

Zhang et al.

(10) Patent No.: US 9,163,010 B2
(45) Date of Patent: Oct. 20, 2015

(54) INDOLINONE PROTEIN KINASE INHIBITORS

(75) Inventors: Don Zhang, Branford, CT (US); Guojian Xie, Cheshire, CT (US)

(73) Assignee: Beta Pharma, Inc., Princeton, NJ (US)

( * ) Notice: Subject to any disclaimer, the term of this patent is extended or adjusted under 35 U.S.C. 154(b) by 656 days.

(21) Appl. No.: 13/441,813

(22) Filed: Apr. 6, 2012

(65) Prior Publication Data

US 2012/0258995 A1    Oct. 11, 2012

Related U.S. Application Data

(60) Provisional application No. 61/473,724, filed on Apr. 8, 2011.

(51) Int. Cl.
*C07D 413/14* (2006.01)
(52) U.S. Cl.
CPC .................................. *C07D 413/14* (2013.01)

(58) Field of Classification Search
None
See application file for complete search history.

(56) References Cited

U.S. PATENT DOCUMENTS

| | | | |
|---|---|---|---|
| 6,573,293 | B2 | 6/2003 | Tang et al. |
| 2003/0130235 | A1 | 7/2003 | Mattson et al. |
| 2005/0171357 | A1 | 8/2005 | Jin et al. |

OTHER PUBLICATIONS

Jantzen. Modern Pharmaceutics, 1996, p. 596.*

* cited by examiner

*Primary Examiner* — Noble Jarrell
(74) *Attorney, Agent, or Firm* — Fox Rothschild LLP; Wansheng Jerry Liu

(57) ABSTRACT

The present invention relates to new indolinone compounds and their pharmaceutically acceptable salts and prodrugs for treating and preventing VEGFR related cellular disorders such as cancer.

20 Claims, No Drawings

INDOLINONE PROTEIN KINASE INHIBITORS

CROSS-REFERENCE

This application claims priority under 35 U.S.C. §119(e) to U.S. Provisional application Ser. No. 61/473,724, filed Apr. 8, 2011, the disclosures of which are incorporated by reference herein in their entirety.

FIELD OF THE INVENTION

The present invention relates to new indolinone compounds which are effective in treating disorders related to abnormal VEGFR-1 (Flt-1), or VEGFR-2 (KDR) activities. Pharmaceutical compositions comprising these compounds, methods of treating diseases utilizing pharmaceutical compositions comprising these compounds and methods of preparing them are also disclosed.

BACKGROUND OF THE INVENTION

VEGFR-1 (Flt-1) and VEGFR-2 (KDR/Flk-1) activities have been linked to cell growth, differentiation and proliferation. The apparent link between VEGFR-1 (Flt-1) and VEGFR-2 (KDR/Flk-1)-related cellular activities and human disorders had generated a great deal of effort to identify ways to modulate their activity and to identify small molecules which act as their inhibitors. For example, sunitinib from U.S. Pat. No. 6,573,293, was developed into a drug product with a tradename Sutent®. However, there are numerous side effects associated with sunitinib therapy, such as fatigue, diarrhea, nausea, anorexia, hypertension, a yellow skin discoloration, hand-foot skin reaction, and stomatitis. Serious (grade 3 or 4) adverse events occur in up to 10% of patients and include hypertension, fatigue, asthenia, diarrhea, and chemotherapy-induced acral erythema. Lab abnormalities associated with sunitinib therapy include lipase, amylase, neutrophils, lymphocytes, and platelets. Hypothyroidism and reversible erythrocytosis have also been associated with sunitinib. Moreover, dose reductions were required in 50% of the patients studied in RCC in order to manage the significant toxicities of sunitinib and its efficacy at dose reduced subgroup has never been published. There is a need to develop new compounds with better toxicity and efficacy profiles for cancer treatment.

BRIEF SUMMARY OF THE INVENTION

The present invention is directed to new indolinone compounds which inhibit VEGFR-1 (Flt-1), and/or VEGFR-2 (KDR) and regulate disorders, such as cancer, related to VEGFR-1 (Flt-1), and/or VEGFR-2 (KDR).

Accordingly, in one aspect, the present invention relates to new indolinones of Formula I:

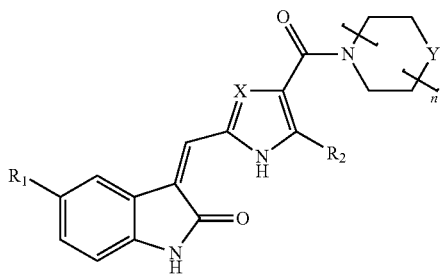

Formula I and its pharmaceutically acceptable salts or prodrugs;

wherein $R_1$ is selected from the group consisting of F, Cl, Br, $CF_3$, $CCl_3$, CN, $SO_2NHR$, COR, CONHR and R; wherein $R_2$=R; wherein X=CH or CR; wherein Y is O, NH or NR; wherein n=2-4; and wherein R is H, alkyl, aryl, alkoxy or aryloxy.

In a second aspect, this invention is directed to a method of synthesizing the compound of formula I by reacting

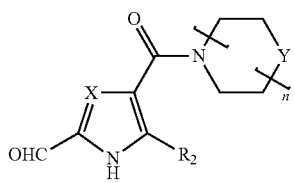

with

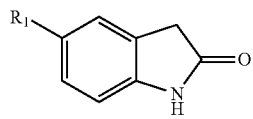

to produce compound of formula I, wherein n=2-4.

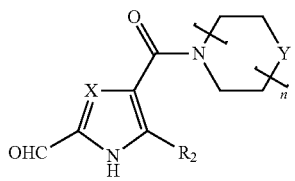

can be prepared by reacting

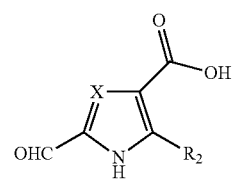

with

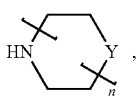

wherein n=2-4.

In a third aspect, this invention is directed to a compound of formula II:

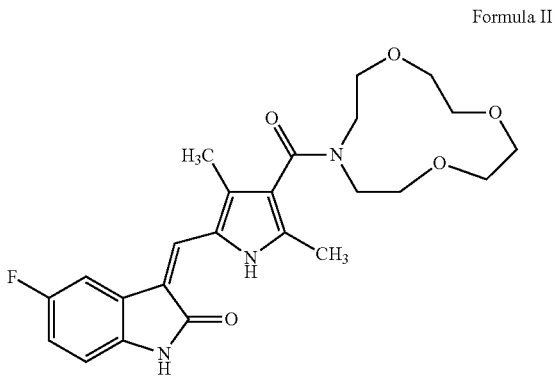 [SMILES: Cc1[nH]c(/C=C2\C(=O)Nc3ccc(F)cc32)c(C)c1C(=O)N1CCOCCOCCOCC1]

Formula II and its pharmaceutically acceptable salts or prodrugs thereof.

Lastly, this invention is also directed to a method of treating or preventing a disorder related to VEGFR, such as VEGFR-1 (Flt-1), or VEGFR-2 (KDR).

DETAILED DESCRIPTION OF THE INVENTION

Definitions

Unless otherwise stated the following terms used in the specification and claims have the meanings discussed below:

"Alkyl" refers to a saturated aliphatic hydrocarbon radical including straight chain and branched chain groups of 1 to 20 carbon atoms. The alkyl group may be substituted or unsubstituted.

"Cycloalkyl" refers to a 3 to 8 member all-carbon monocyclic ring, an all-carbon 5-member/6-member or 6-member/6-member fused bicyclic ring or a multicyclic fused ring (a "fused" ring system means that each ring in the system shares an adjacent pair of carbon atoms with each other ring in the system) group wherein one or more of the rings may contain one or more double bonds but none of the rings has a completely conjugated pi-electron system.

"Aryl" refers to an all-carbon monocyclic or fused-ring polycyclic (i.e., rings which share adjacent pairs of carbon atoms) groups of 1 to 12 carbon atoms having a completely conjugated pi-electron system. Examples, without limitation, of aryl groups are phenyl, naphthalenyl and anthracenyl. The aryl group may be substituted or unsubstituted.

"Alkoxy" refers to both an —O-(unsubstituted alkyl) and an —O-(unsubstituted cycloalkyl) group. Representative examples include, but are not limited to, e.g., methoxy, ethoxy, propoxy, butoxy, cyclopropyloxy, cyclobutyloxy, cyclopentyloxy, cyclohexyloxy, and the like.

"Aryloxy" refers to both an —O-aryl and an —O-heteroaryl group, as defined herein. Representative examples include, but are not limited to, phenoxy, pyridinyloxy, furanyloxy, thienyloxy, pyrimidinyloxy, pyrazinyloxy, and the like, and derivatives thereof.

"Halo" group refers to fluorine, chlorine, bromine or iodine, preferably fluorine or chlorine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

The compounds of Formula I may exhibit the phenomena of tautomerism and structural isomerism. For example, the compounds described herein may adopt an E or a Z configuration about the double bond connecting the 2-indolinone moiety to the pyrrole moiety or they may be a mixture of E and Z. This invention encompasses any tautomeric or structural isomeric form and mixtures thereof which possess the ability to modulate VEGFR, such as VEGFR-1 (Flt-1), and/or VEGFR-2 (KDR) activity and is not limited to any one tautomeric or structural isomeric form.

A "pharmaceutical composition" refers to a mixture of one or more of the compounds described herein, or physiologically/pharmaceutically acceptable salts or prodrugs thereof, with other chemical components, such as physiologically/pharmaceutically acceptable carriers and excipients. The purpose of a pharmaceutical composition is to facilitate administration of a compound to an organism.

The compound of Formula I may also act as a prodrug. A "prodrug" refers to an agent which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but then is metabolically hydrolyzed to the carboxylic acid, the active entity, once inside the cell where water solubility is beneficial.

Additionally, it is contemplated that a compound of Formula I would be metabolized by enzymes in the body of the organism such as human being to generate a metabolite that can modulate the activity of the protein kinases. Such metabolites are within the scope of the present invention.

As used herein, a "physiologically/pharmaceutically acceptable carrier" refers to a carrier or diluent that does not cause significant irritation to an organism and does not abrogate the biological activity and properties of the administered compound.

A "pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols. As used herein, the term "pharmaceutically acceptable salt" refers to those salts which retain the biological effectiveness and properties of the parent compound.

"Method" refers to manners, means, techniques and procedures for accomplishing a given task including, but not limited to, those manners, means, techniques and procedures either known to, or readily developed from known manners, means, techniques and procedures by, practitioners of the chemical, pharmaceutical, biological, biochemical and medical arts.

"Modulation" or "modulating" refers to the alteration of the catalytic activity of a receptor tyrosine kinase, VEGFR (or VGFR), including, but not limited to all three VEGFR (VGFR) isoforms identified in humans; VEGFR-1 (Flt-1), VEGFR-2 (KDR) and VEGFR-3 (Flt-4).

"VEGFR" or "VGFR" refers to vascular endothelial growth factor, a member of the tyrosine kinase growth factor receptor family. VEGF is believed to plan an essential role in vasculogenesis and angiogenesis.

"In vitro" refers to procedures performed in an artificial environment such as, e.g., without limitation, in a test tube or culture medium.

"In vivo" refers to procedures performed within a living organism such as, without limitation, a mouse, rat or rabbit.

"Treat", "treating" and "treatment" refer to a method of alleviating or abrogating a PK mediated cellular disorder and/or its attendant symptoms. With regard particularly to cancer, these terms simply mean that the life expectancy of an individual affected with a cancer will be increased or that one or more of the symptoms of the disease will be reduced.

"Organism" refers to any living entity comprised of at least one cell. A living organism can be as simple as, for example, a single eukaryotic cell or as complex as a mammal, including a human being.

"Therapeutically effective amount" refers to that amount of the compound being administered which will relieve to some extent one or more of the symptoms of the disorder being treated. In reference to the treatment of cancer, a therapeutically effective amount refers to that amount which has the effect of:

(1) reducing the size of the tumor;
(2) inhibiting (that is, slowing to some extent, preferably stopping) tumor metastasis;
(3) inhibiting to some extent (that is, slowing to some extent, preferably stopping) tumor growth, and/or,
(4) relieving to some extent (or, preferably, eliminating) one or more symptoms associated with the cancer.

Representative compounds of the present invention are shown in Table I below.

TABLE 1

Compound of formula II

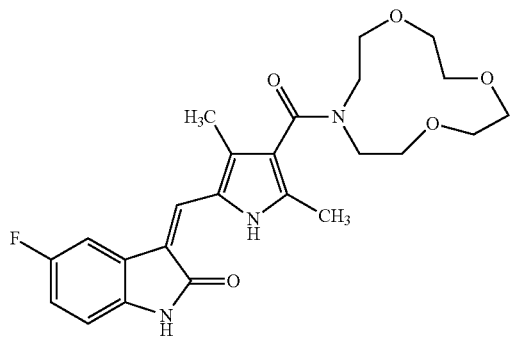 [SMILES: Cc1[nH]c(/C=C2\C(=O)Nc3ccc(F)cc32)c(C)c1C(=O)N1CCOCCOCCOCC1]

Compound of formula III

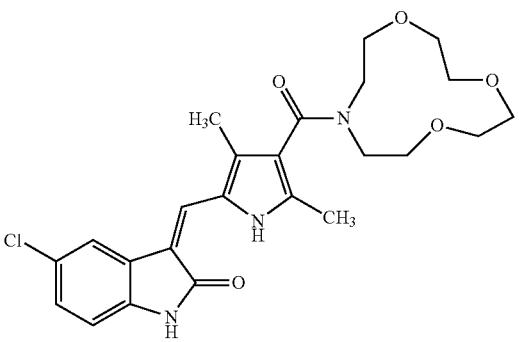 [SMILES: Cc1[nH]c(/C=C2\C(=O)Nc3ccc(Cl)cc32)c(C)c1C(=O)N1CCOCCOCCOCC1]

TABLE 1-continued
Compound of formula IV
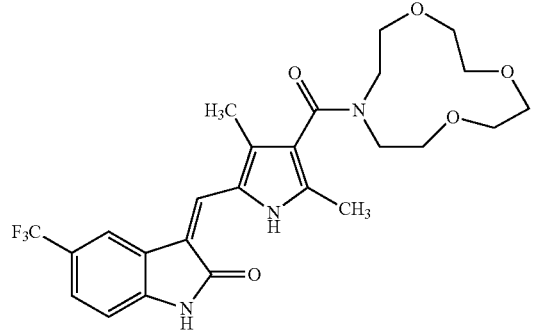 [SMILES: Cc1[nH]c(/C=C2\C(=O)Nc3ccc(C(F)(F)F)cc32)c(C)c1C(=O)N1CCOCCOCCOCC1]
Compound of formula V
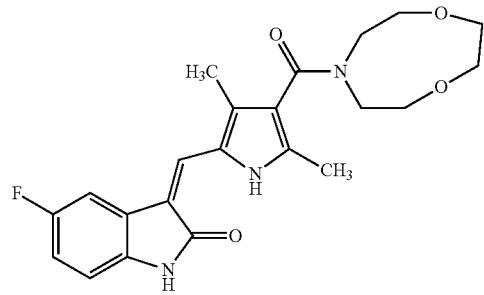 [SMILES: Cc1[nH]c(/C=C2\C(=O)Nc3ccc(F)cc32)c(C)c1C(=O)N1CCOCCOCC1]
Compound of formula VI
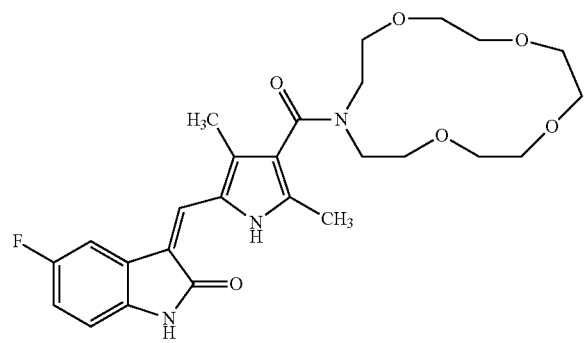 [SMILES: Cc1[nH]c(/C=C2\C(=O)Nc3ccc(F)cc32)c(C)c1C(=O)N1CCOCCOCCOCCOCC1]
Compound of formula VII
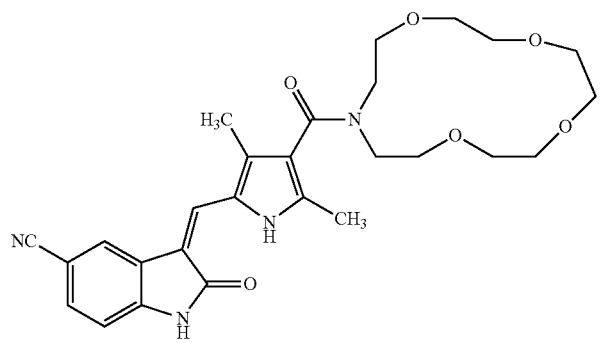 [SMILES: Cc1[nH]c(/C=C2\C(=O)Nc3ccc(C#N)cc32)c(C)c1C(=O)N1CCOCCOCCOCCOCC1]

TABLE 1-continued
Compound of formula VIII
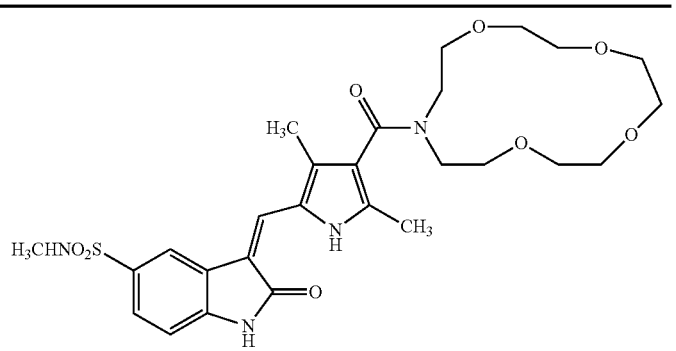
Compound of formula IX
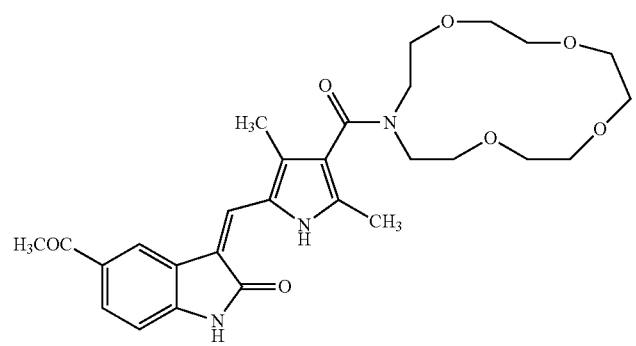 [SMILES: CC(=O)c1ccc2c(c1)/C(=C/c1[nH]c(C)c(C(=O)N3CCOCCOCCOCCOCC3)c1C)C(=O)N2]
Compound of formula X
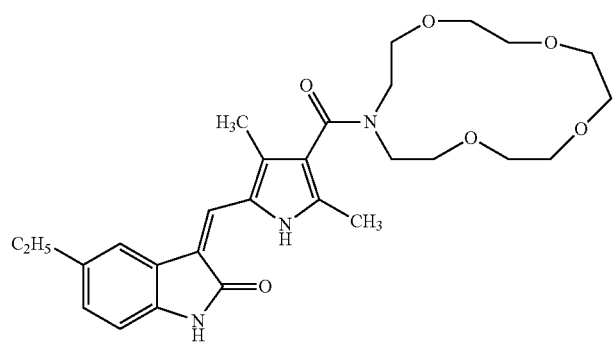
Compound of formula XI
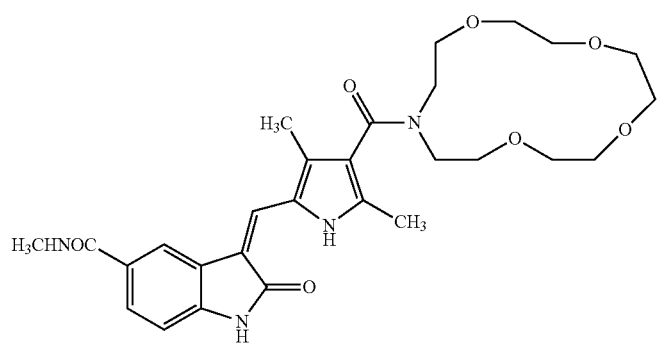

TABLE 1-continued
Compound of formula XII
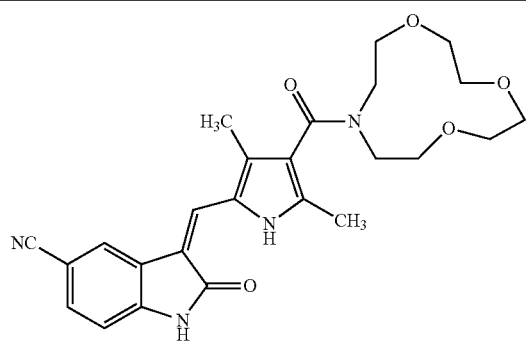
Compound of formula XIII
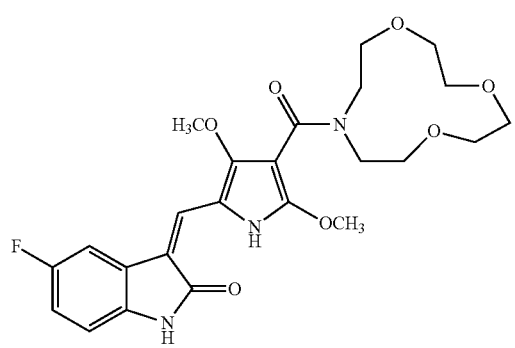 [SMILES: COc1[nH]c(/C=C2\C(=O)Nc3ccc(F)cc32)c(OC)c1C(=O)N1CCOCCOCCOCC1]
Compound of formula XIV
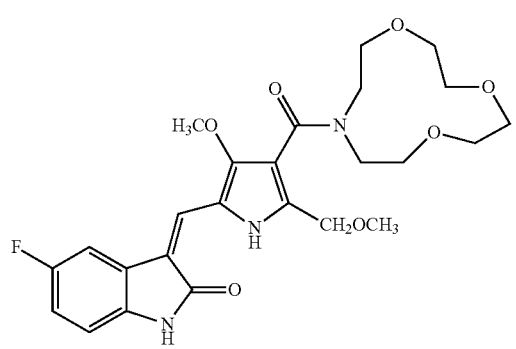
Compound of formula XV
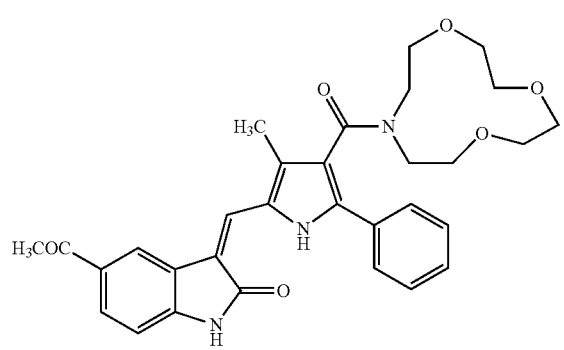 [SMILES: CC(=O)c1ccc2c(c1)/C(=C/c1[nH]c(-c3ccccc3)c(C(=O)N3CCOCCOCCOCC3)c1C)C(=O)N2]

TABLE 1-continued

Compound of formula XVI

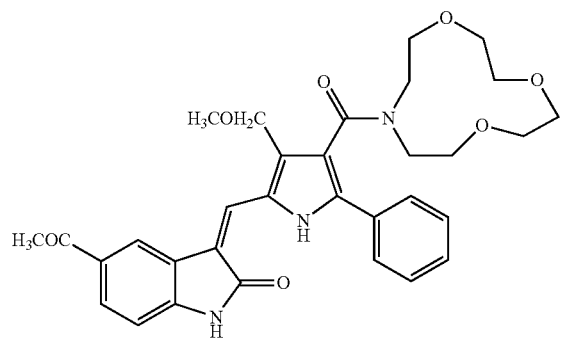

Preferred Embodiments

While the broadest definition is set forth in the Summary of the Invention, certain compounds of Formula I set forth below are preferred. A preferred group of compounds of Formula I is that wherein $R_1$ is F, Cl, or Br, and more preferably $R_1$ is F. Another preferred group of compounds of formula I is that wherein X is CR and R is alkyl, more preferably R is methyl. Another preferred group of compounds of formula I is that wherein Y is O, and preferably n is 3.

In another embodiment of the synthesis process, $R_1$ is F, Cl, or Br, preferably $R_1$ is F. X is preferably CR, wherein R is alkyl, preferably R is methyl. Y is preferably O and n is 3.

In another embodiment of the present invention, the disorders to be treated are related to VEGFR, such as VEGFR-1 (Flt-1), or VEGFR-2 (KDR). Preferably, the disorder is a cancer selected from the group consisting of squamous cell carcinoma, astrocytoma, Kaposi's sarcoma, glioblastoma, lung cancer, bladder cancer, head and neck cancer, melanoma, ovarian cancer, prostate cancer, breast cancer, small-cell lung cancer, glioma, colorectal cancer, genitourinary cancer and gastrointestinal cancer.

The following preparations and examples are given to enable those skilled in the art to more clearly understand and to practice the present invention. They should not be considered as limiting the scope of the invention, but merely as being illustrative and representative thereof.

General Synthetic Procedures to Prepare the Compounds of this Invention:

General Synthesis Procedure 1:

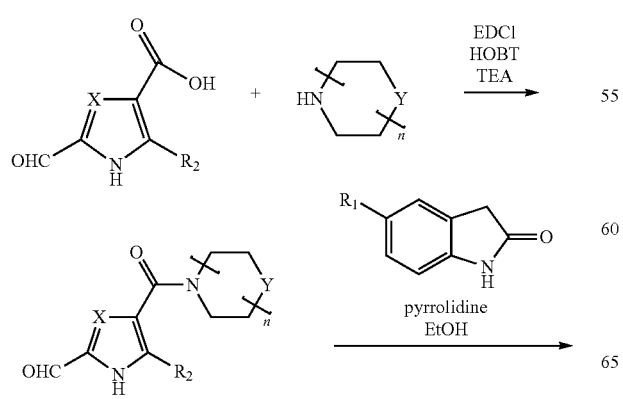

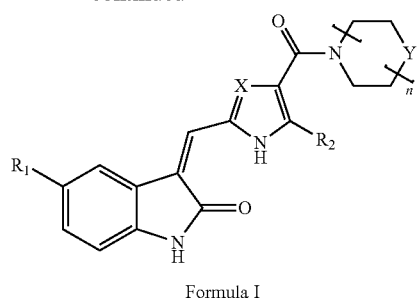

Formula I

General Synthesis Procedure 2:

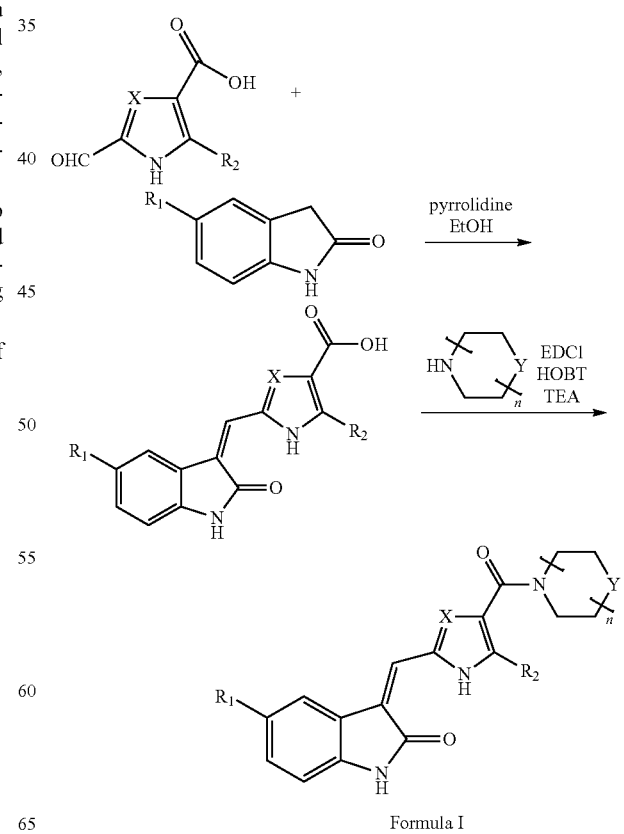

Formula I

It will be clear to those skilled in the art, based both on known general principles of organic synthesis and on the disclosures herein which base would be most appropriate for the reaction contemplated.

The solvent in which the reaction is carried out may be water, alcohols, acetone, pentane, hexane, benzene, toluene, methylene chloride and carbon tetrachloride. Examples of polar aprotic solvents are chloroform, tetrahydrofuran, dimethylsulfoxide and dimethylformamide.

The reaction is carried out at temperatures greater than room temperature. The temperature is generally from about 30° C. to about 150° C., preferably about 80° C. to about 100° C., most preferable about 75° C. to about 85° C., which is about the boiling point of ethanol. By "about" is meant that the temperature range is preferably within 10 degrees Celsius of the indicated temperature, more preferably within 5° C. of the indicated temperature and, most preferably, within 2° C. of the indicated temperature. Thus, for example, by "about 75° C." is meant 75° C.±10° C., preferably 75° C.±5° C. and most preferably, 75° C.±2° C.

Example 1

General Procedures for Synthesizing Compound of Formula II

Procedure 1:

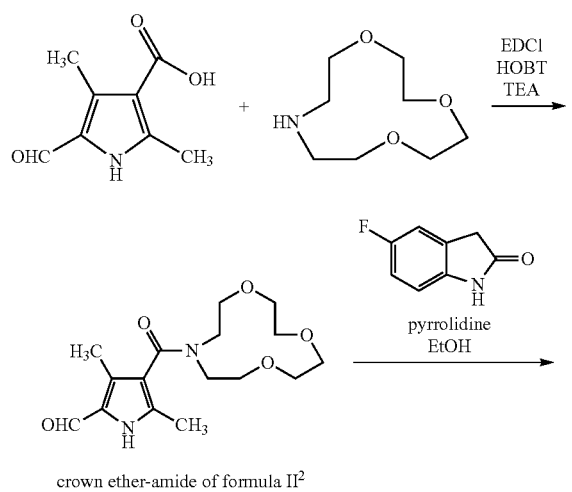

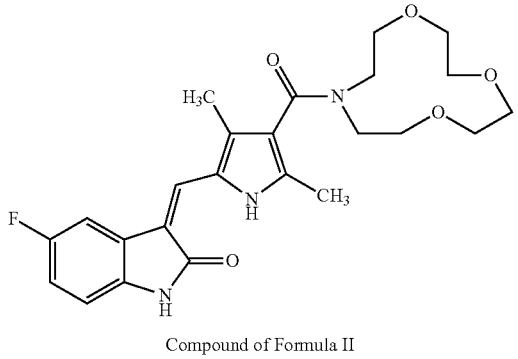

Compound of Formula II

Procedure 2:

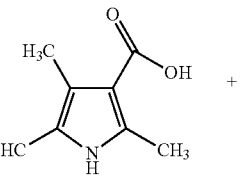

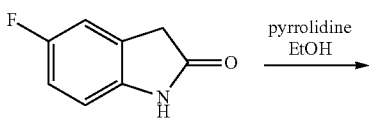

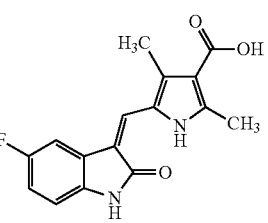 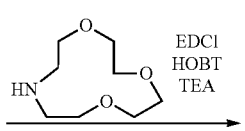

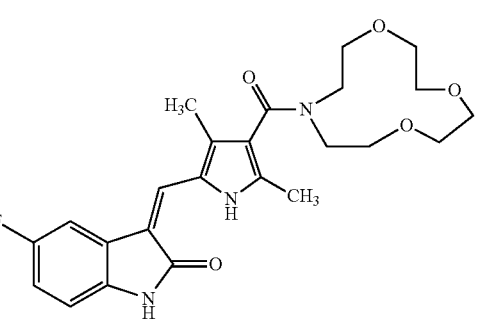

Compound of formula II

Example 2

Preparation of the Compound of Formula II 5-fluoroindolin-2-one (151.04 mg, 1.0 mmol) was dissolved in ethanol (30 ml) at room temperature. To this solution was added pyrrolidine (152.24 mg, 2.0 mmol). The resulting solution was stirred for 1 hr and then cooled down to 0° C. To this solution was added the crown ether-amide of formula II[2] (324.17 mg, 1.0 mmol) in ethanol (20 ml) dropwise over 30 min. The mixture was stirred at room temperature overnight. It was then heated to reflux for 2 hr. TLC (ethyl acetate/dichloromethane: 30/70) indicated the completion. It was concentrated to give a brown residue which was chromatographed on a column of silica gel (ethyl acetate/dichloromethane: 2/8) to give compound of formula II as a red solid: 348.4 mg (76.2%).

$^1$H NMR (DMSO) δ13.56 (s, 1H), 10.85 (s, broad, 1H), 7.75 (d, 1H), 7.68 (s, 1H), 6.93 (t, 1H), 6.85 (m, 1H), 3.35-3.77 (m, 14H), 2.55 (m, 2H), 2.28 (s, 3H), 2.23 (s, 3H); ES-MS m/z 458 (MH$^+$).

Example 3

Synthesis of Compound of Formula III

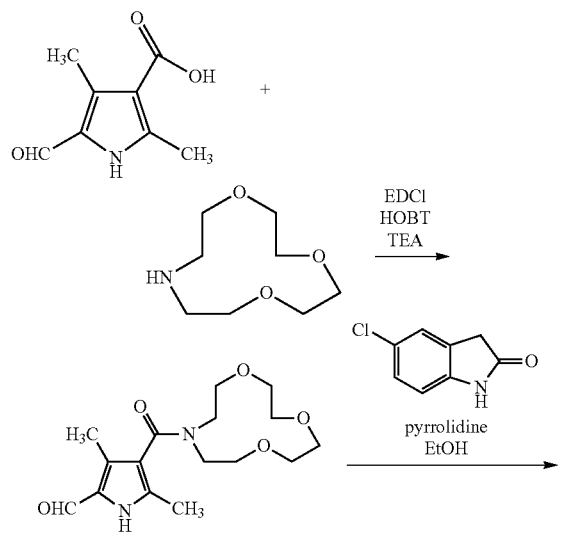

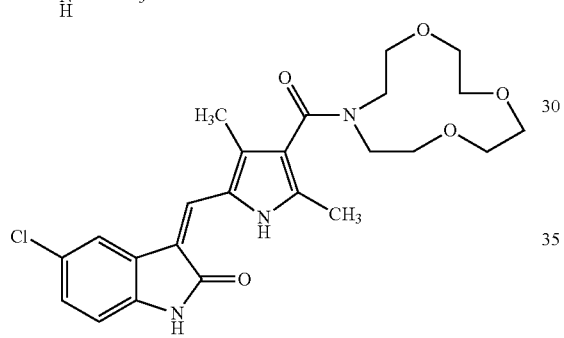

Compound of Formula III 5-chloroindolin-2-one (163 mg, 1 mmol) is dissolved in ethanol (30 ml) at room temperature. To this solution was added pyrrolidine (152 mg, 2 mmol). The resulting solution is stirred for 1-3 hrs and then cooled down to 0° C. To this solution is added the crown ether-amide (324 mg, 1 mmol) in ethanol (20 ml) dropwise over 30-60 minutes. The mixture is stirred at room temperature overnight. It is then heated to reflux for about 2-3 hrs. TLC (ethyl acetate/dichloromethane: 30/70) indicated the completion. It is concentrated to give compound of formula III.

Example 4

Synthesis of Compound of Formula IV

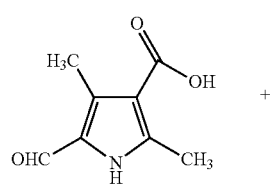

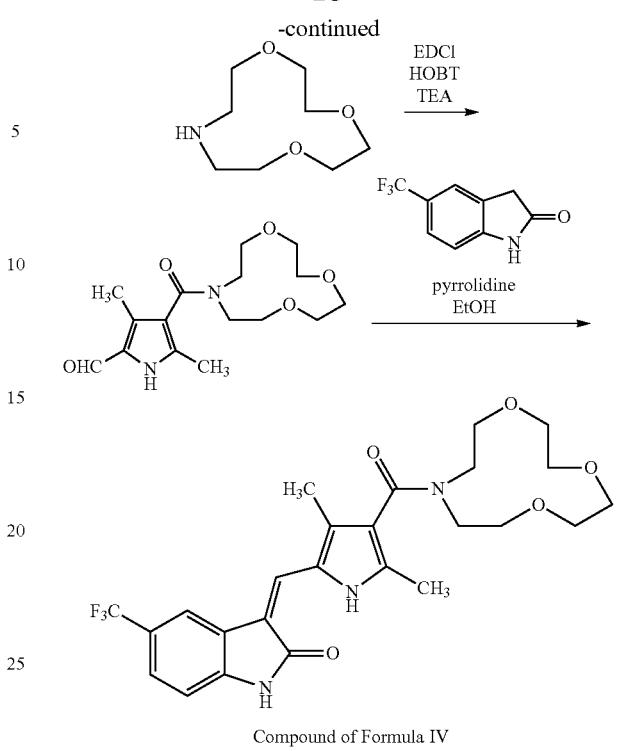

Compound of Formula IV 5-trifluoromethylindolin-2-one (201 mg, 1 mmol) is dissolved in ethanol (30 ml) at room temperature. To this solution was added pyrrolidine (152 mg, 2 mmol). The resulting solution is stirred for 1-2 hrs and then cooled down to about 0° C. To this solution is added the crown ether-amide (324 mg, 1 mmol) in ethanol (20 ml) dropwise over 30-60 minutes. The mixture is stirred at room temperature overnight. It is then heated to reflux for about 2-3 hrs. TLC (ethyl acetate/dichloromethane: 30/70) indicated the completion. It is concentrated to give compound of formula IV.

Example 5

Synthesis of Compounds of Formulas V-XVI

Compounds of formulas V-XVI are prepared following similar procedures of examples 1-4.

Example 6

Comparative Study of the Compound of Formula II and Sunitinib

The effects of compound of formula II on inhibiting VEGFR were compared against that of sunitinib in vitro. The enzymatic activities ($IC_{50}$) are summarized in Table 2 below.

TABLE 2

| | Enzymatic Activities $IC_{50}$ (nM) | | |
|---|---|---|---|
| Compound | VEGFR-1 (Flt-1) or VGFR1 FLT1 | VEGFR-2 KDR or VGFR2 KDR | VEGFR-3 (Flt-4) or VGFR3 FLT4 |
| Formula II | 40 | 2.5 | No Inhibition |
| Sunitinib | N/A | 10 | No Inhibition |

Without intending to be bound by any particular theory of operation, it is believed that the compounds of formula I (when n is 3) undergo the following metabolism-driven modification to their crown ether side chain:

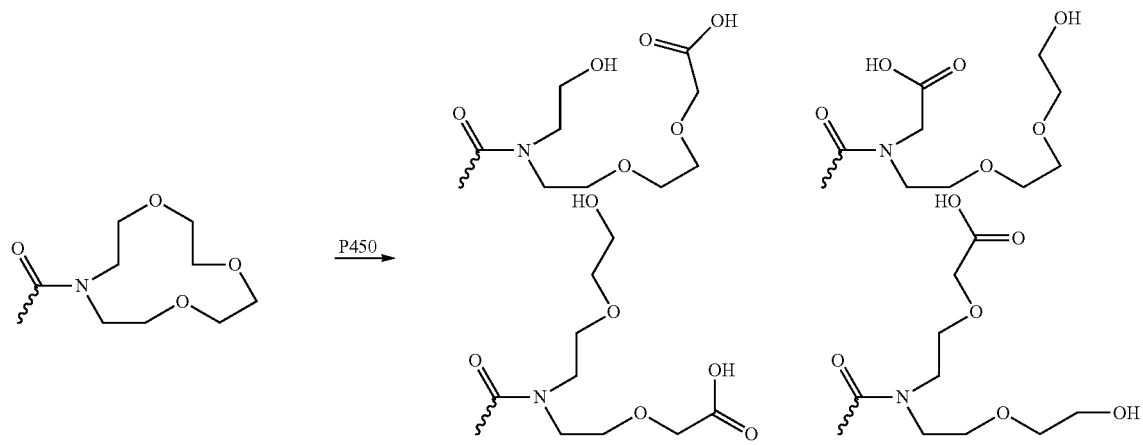

At present, the therapeutically effective amounts of compounds of Formula I may range from approximately 5 mg/day to 1500 mg/per day; preferably about 10 mg to 1,000 mg/day. Even more preferably 25 mg to 800 mg/day.

A compound, salt or prodrug of this invention can also be used in combination with other antimetabolite chemotherapeutic agents such as, without limitation, folic acid analogs, e.g. methotrexate (used in the treatment of acute lymphocytic leukemia, choriocarcinoma, mycosis fungiodes breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

It is contemplated that a compound, salt or prodrug of this invention can also be used in combination with natural product based chemotherapeutic agents. One skilled in the art would readily appreciate that the present invention is well adapted to carry out the objects and obtain the ends and advantages mentioned, as well as those inherent herein. The molecular complexes and the methods, procedures, treatments, molecules, specific compounds described herein are presently representative of preferred embodiments, are exemplary, and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. Other embodiments are within the following claims.

What is claimed:
1. A compound of Formula (I):

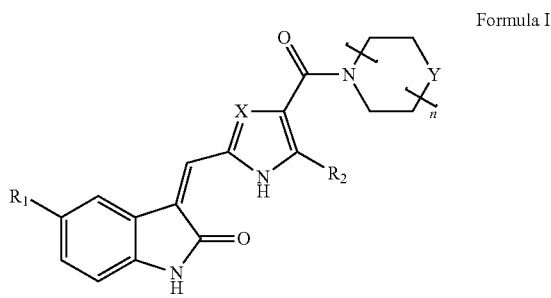

Formula I or a pharmaceutically acceptable salt thereof;
wherein $R_1$ is selected from the group consisting of F, Cl, Br, $CF_3$, $CCl_3$, CN, $SO_2NHR$, COR, CONHR and R;
wherein $R_2$=R;
wherein X=CH or CR;
wherein Y is O, NH or NR;
wherein n=2-4; and
wherein R is H, alkyl, aryl, alkoxy or aryloxy.

2. The compound of claim 1, or a pharmaceutically acceptable salt thereof, wherein $R_1$ is F, Cl, or Br.

3. The compound of claim 1, or a pharmaceutically acceptable salt thereof, wherein $R_1$ is F.

4. The compound of claim 3, or a pharmaceutically acceptable salt thereof, wherein X is CR and R is alkyl.

5. The compound of claim 4, or a pharmaceutically acceptable salt thereof, wherein R is methyl.

6. The compound of claim 5, or a pharmaceutically acceptable salt thereof, wherein Y is O.

7. A method of synthesizing the compound of claim 1, or a pharmaceutically acceptable salt thereof, comprising the step of reacting

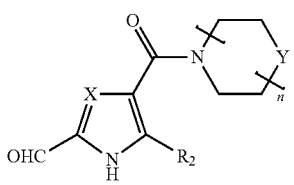

with

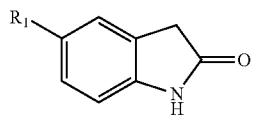

to form compound of formula I, wherein n=2-4.

8. The method of claim 7, further comprising the step of reacting

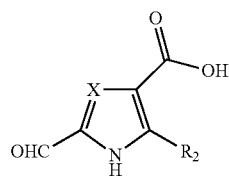

with

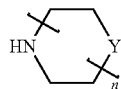

to form

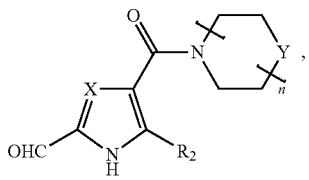

wherein n=2-4.

9. The method of claim 8, wherein $R_1$ is F, Cl, or Br.

10. The method of claim 9, wherein $R_1$ is F.

11. The method of claim 7, wherein X is CR and R is alkyl.

12. The method of claim 11, wherein R is methyl.

13. The method of claim 7, wherein Y is O.

14. The method of claim 7, wherein $R_1$ is F; X is CR; R is methyl; Y is O.

15. The method of claim 14, wherein n is 3.

16. A compound of formula II:

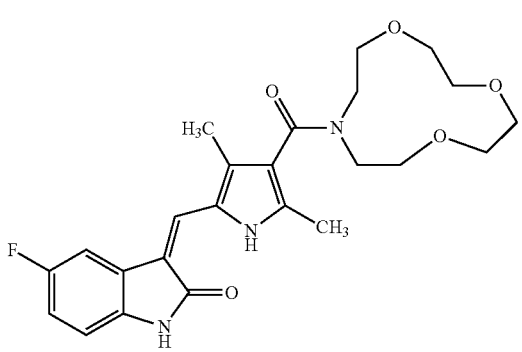

Formula II or a pharmaceutically acceptable salt thereof.

17. A pharmaceutical composition, comprising a compound of claim 1, or a pharmaceutically acceptable salt thereof, and a pharmaceutically acceptable carrier or excipient.

18. A pharmaceutical composition, comprising the compound of claim 16, or a pharmaceutically acceptable salt thereof, and a pharmaceutically acceptable carrier or excipient.

19. A method of treating a disorder related to VEGFR, comprising administering to a subject in need thereof a therapeutically effective amount of the compound of claim 1, or a pharmaceutically acceptable salt or composition thereof, wherein said disorder is selected from the group consisting of lung cancer, colorectal cancer, and gastrointestinal cancer.

20. The method of claim 19, wherein said disorder is small-cell lung cancer.

* * * * *